US009664636B2

(12) United States Patent
Wen et al.

(10) Patent No.: US 9,664,636 B2
(45) Date of Patent: May 30, 2017

(54) CHLORINE DETECTION WITH PULSED AMPEROMETRIC DETECTION

(71) Applicant: Thermo Fisher Scientific Aquasensors LLC, Waltham, MA (US)

(72) Inventors: Xiaowen Wen, Lexington, MA (US); Arthur E. Tobey, Salem, NH (US)

(73) Assignee: Thermo Fisher Scientific Aquasensors LLC, Waltham, MA (US)

( * ) Notice: Subject to any disclaimer, the term of this patent is extended or adjusted under 35 U.S.C. 154(b) by 514 days.

(21) Appl. No.: 14/138,933

(22) Filed: Dec. 23, 2013

(65) Prior Publication Data
US 2015/0177173 A1    Jun. 25, 2015

(51) Int. Cl.
*G01N 27/40* (2006.01)
*G01N 27/26* (2006.01)
*G01N 27/404* (2006.01)

(52) U.S. Cl.
CPC ......... *G01N 27/26* (2013.01); *G01N 27/4045* (2013.01)

(58) Field of Classification Search
CPC .... G01N 27/304; G01N 27/31; G01N 27/404; G01N 27/4045; G01N 27/413; G01N 27/4166; G01N 27/4168; G01N 27/48; G01N 33/18; G01N 33/182
See application file for complete search history.

(56) References Cited

U.S. PATENT DOCUMENTS

| 4,939,924 | A | 7/1990 | Johnson et al. |
| 2005/0029103 | A1 | 2/2005 | Feng et al. |
| 2012/0216605 | A1* | 8/2012 | Silveri ............... G01N 27/4168 73/61.41 |
| 2013/0334063 | A1* | 12/2013 | Rosenblatt ........... G01N 27/417 205/778.5 |

FOREIGN PATENT DOCUMENTS

| FR | 2778463 | 11/1999 |
| JP | S62153740 A | 7/1987 |
| WO | 2013014187 A1 | 1/2013 |

OTHER PUBLICATIONS

Austin-Harrison et al., "Pulsed Amperometric Detection Based on Direct and Indirect Anodic Reactions: A Review," Electroanalysis, 1, 189-197, 1989.
(Continued)

*Primary Examiner* — J. Christopher Ball
(74) *Attorney, Agent, or Firm* — Wood Herron & Evans LLP

(57) ABSTRACT

A method of measuring oxidant in an aqueous composition using an electrode system comprising a membrane permeable to a species to be measured, a cathode situated behind the membrane, and an electrolyte between the membrane and cathode. Embodiments of the method may include contacting the membrane and an anode with the aqueous composition, and measuring the current between the cathode and anode in response to a first voltage applied between them. A pulse of a second voltage may be applied between the cathode and the anode, where the second voltage is different from the first voltage. Apparatus and computer program products which may perform the method, are also provided.

16 Claims, 7 Drawing Sheets

(56) References Cited

OTHER PUBLICATIONS

Coutinho et al., "Development of Instrumentation for Amperometric and Coulometric Detection using Ultramicroelectrodes," J. Braz. Chem. Soc., 19(1), 131-139, 2008.
Damlin et al., "Characterization of Hardwood-derived Carboxymethylcellulose by High pH Anion Chromatography Using Pulsed Amperometric Detection," Cellulose Chem. Technol., 44(1-3), 65-69, 2010.
Handbook of Ion Chromatography, 3rd completely revised and updated edition, 2004 WILEY-VCH Verlag GmbH & Co., KGaA, Weinheim, ISBN: 3-527-28701-9 (see section 7.1.2 "Amperometric Detection").
Huntley and Malkov, "Amperometric Probes or DPD Analyzers: Which is Best for On-Line Chlorine Monitoring?," WaterWorld, Editorial Feature, 2 pages, 2009.
Johnson et al., "Chromatography with Pulsed Electrochemical Detection at Gold and Platinum Electrodes," Anal. Chem., 62(10), 589 A-596 A, 1990.
Lacourse, "Pulsed Electrochemical Detection: Waveform Evolution," Chromatography Online.com, 11 pages, Jul. 1, 2011.
Malkov et al., "Comparison of On-line Chlorine Analysis Methods and Instrumentation Built on Amperometric and Coloimetric Technologies," American Water Works Assocation, 22 pages, copyright 2009.
Neuburger et al., "Pulsed Amperometric Detection of Carbohydrates at Gold Electrodes with a Two-Step Potential Waveform," Anal. Chem., 59, 150-154, 1987.
Waters 2465 Electrochemical Detector, Operator's Guide, 71500246502, Rev. B, 226 pages, copyright 2002, 2007.
Great Britain Intellectual Property Office, Corresponding GB Patent Application No. 14229652, Search Report Under Section 17, Sep. 28, 2015, 2 pages.

\* cited by examiner

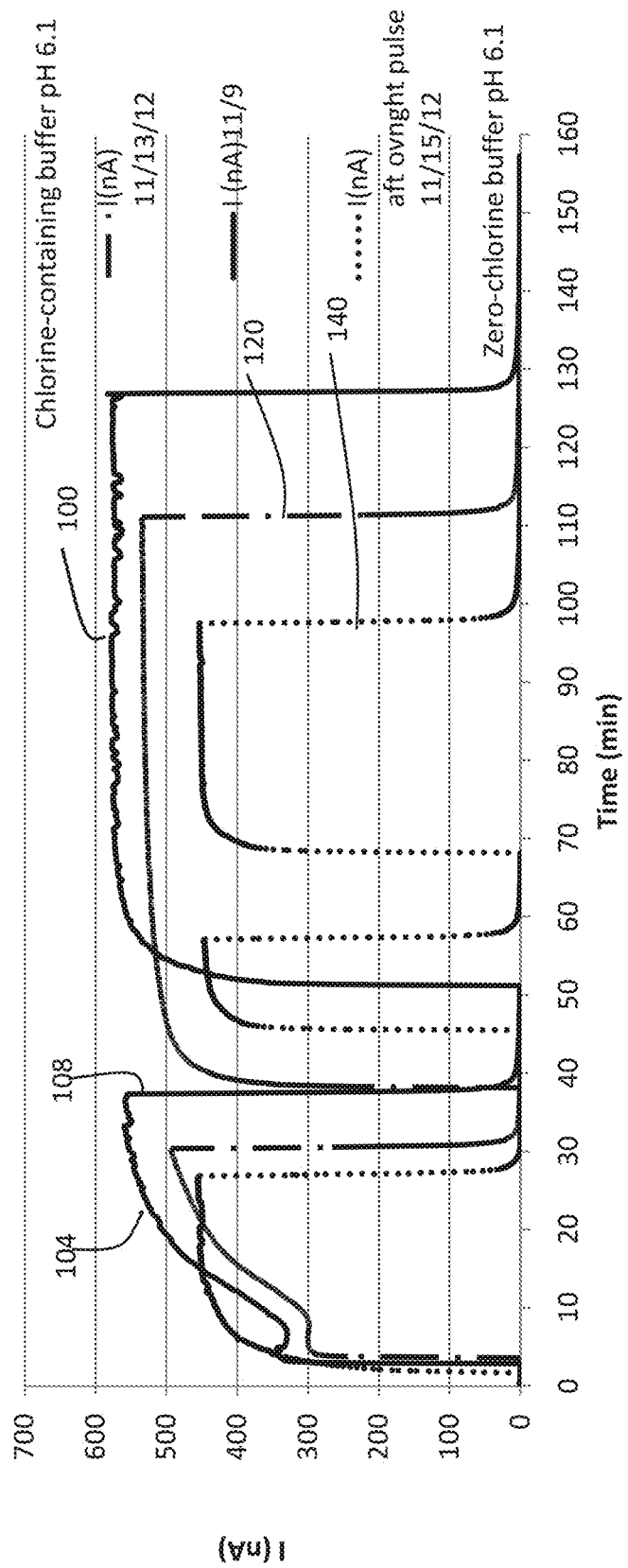

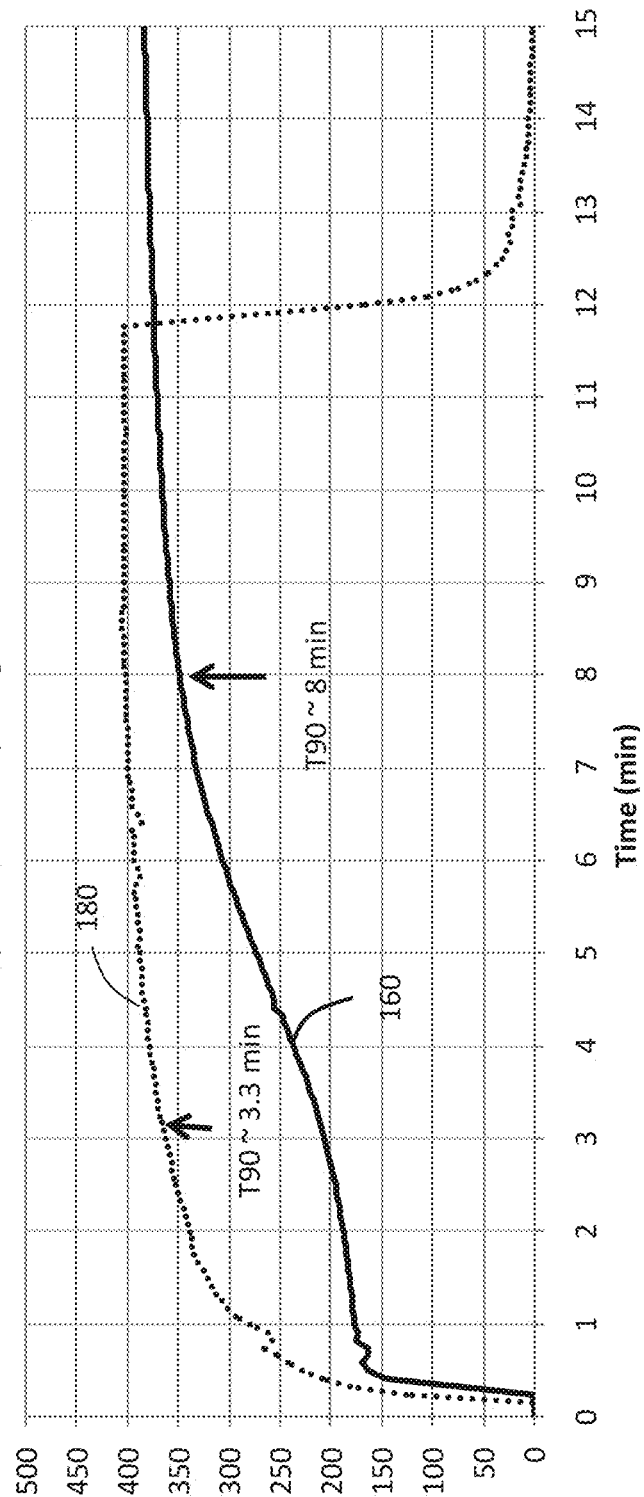

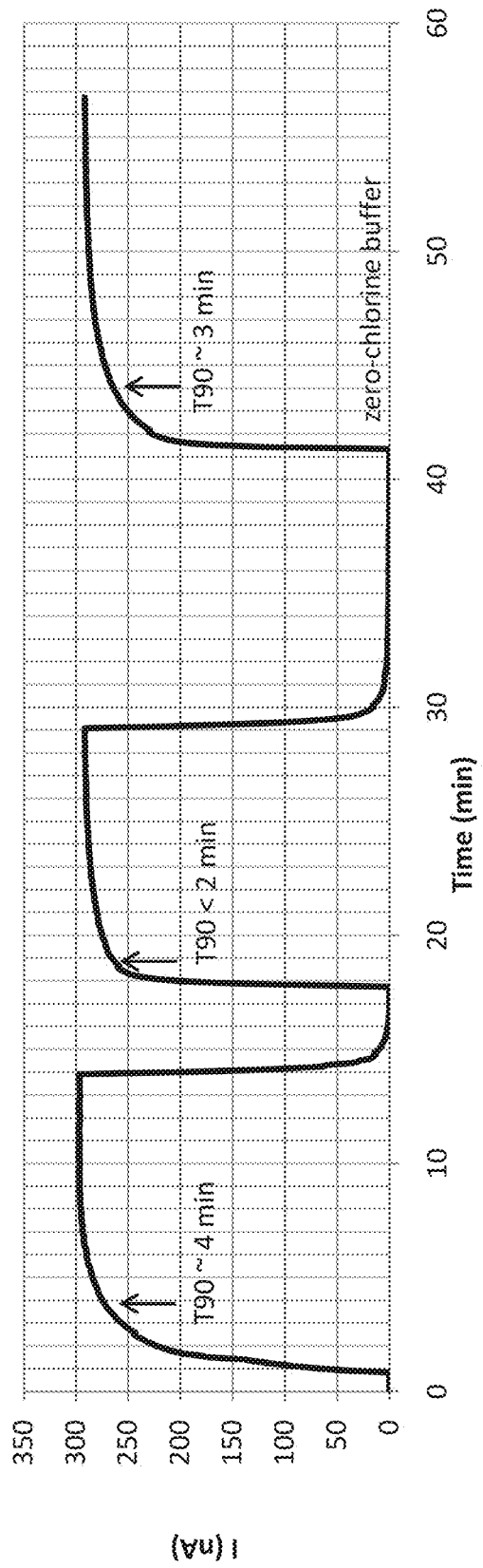

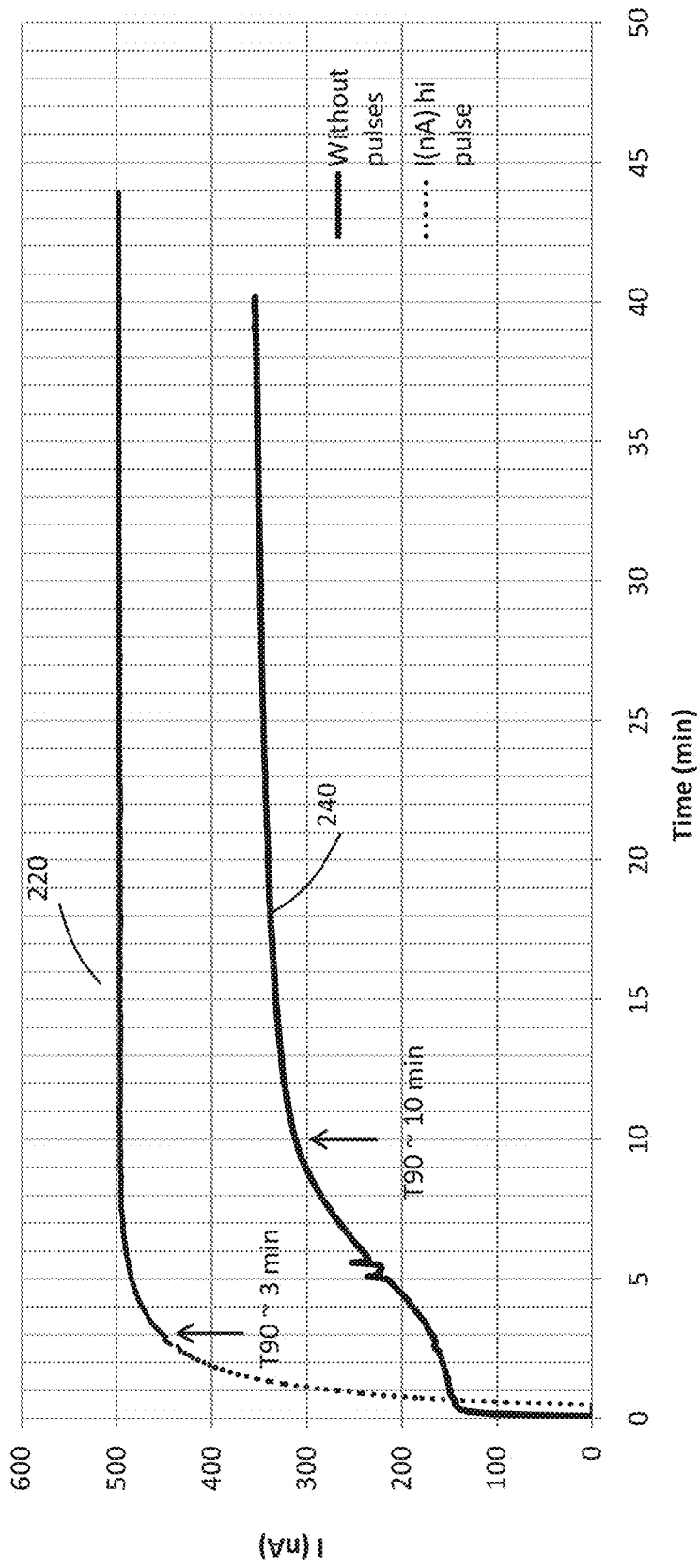

CHLORINE DETECTION WITH PULSED AMPEROMETRIC DETECTION

FIELD

This invention generally relates to detecting a component by amperometric detection.

BACKGROUND

Detecting the presence and concentration of different chemical species using amperometry is a very well known technique. Basically, a voltage appropriate for the species to be detected is applied between two electrodes in communication with a fluid possibly containing that species. The voltage is selected which is sufficient to cause oxidation or reduction of the species to be detected but ideally not any other species in the fluid. The resulting current between the electrodes in response to the applied voltage can then provide an indication of the presence or concentration of the species to be detected. In coulometry the total current over a period of time is measured. In the present application "amperometry" will be used to include methods such as coulometry or voltammetry. Descriptions of amperometry and methods, including selection of the appropriate voltage, are widely available in references including the following and references cited therein: (i) *Handbook of Ion Chromatography, Third Completely Revised Edition,* 2004 WILEY-VCH Verlag GmbH & Co. KGaA, Weinheim, ISBN: 3-527-28701-9 (see section 7.1.2 "Amperometric Detection"); (ii) "Pulsed Amperometric Detection Based on Direct and Indirect Anodic Reactions: A Review", Electroanalysis, 1 (1989) 189-197; (iii) "Development of Instrumentation for Amperometric and Coulometric Detection using Ultramicroelectrodes", *J. Braz. Chem. Soc., Vol.* 19, No. 1, 131-139, 2008.

Amperometry has been used to detect a large variety of organic species. Additionally, amperometry has also been used to detect chlorine in aqueous compositions, such as described in "Comparison of On-line Chlorine Analysis Methods and Instrumentation Built on Amperometric and Colorimetric Technologies", 2009, available from the American Water Works Association, and French patent FR2778463.

In cases involving the oxidation of aliphatic organic compounds at an anode, where the electrolyte is in direct contact with the anode and cathode, it has been recognized that the anode can become fouled—see for example "Liquid Chromatography with Pulsed Electrochemical Detection at Gold and Platinum Electrodes", *Analytical Chemistry,* Vol. 62, No. 10, May 15.1990. In that situation a technique known as pulsed amperometric detection has been used in which a reading potential is applied, followed by a large positive potential to oxidatively desorb adsorbed hydrocarbons, then followed by a large negative potential to cathodically dissolve oxides.

SUMMARY

The present invention recognizes that amperometric detection can be used to detect oxidants (such as chlorine) by reduction at a cathode positioned behind a membrane. The membrane may be selectively permeable to one or more detectable components, for example, an oxidant. Such oxidants can include chlorine in the form of hypochlorous acid (HOCl) or hypochlorite anion (ClO$^-$) or in the combined form of chloramines. Other oxidants can include other halogens such as bromine in the form of hypobromous acid, hypobromite, or bromoamines. Some embodiments of the present invention further recognize that even in this situation, where reduction rather than oxidation is used to detect a species such as free chlorine, and the cathode is behind a membrane, performance of the system may still be adversely affected. Furthermore, some embodiments of the present invention recognize that performance may even be adversely affected where the electrode system is exposed to a chlorine-free composition before being exposed to a chlorine containing composition.

The present invention provides, in one embodiment, a method of measuring a component, such as an oxidant (for example, chlorine) in an aqueous composition. Such embodiments may use an electrode system and membrane. The membrane is permeable to the species to be measured, such as chlorine in the form of hypochlorous acid (HOCl) or hypochlorite anion (ClO$^-$) or in the combined form of chloramines. A cathode is situated behind the membrane, and an electrolyte is disposed between the membrane and cathode. The electrolyte may contain components that facilitate chemical reactions and equilibriums for the electrochemical detection. This embodiment of the method may include contacting the membrane and an anode with the aqueous composition and measuring the current between the cathode and anode in response to a first voltage applied between them. Additionally, a pulse of a second voltage is applied between the cathode and the anode, where the second voltage is different from the first voltage.

Another embodiment provides an apparatus for measuring a component as described above, such as chlorine in an aqueous solution. Such an apparatus may include an electrode system comprising an electrolyte chamber defined at least in part by a membrane of a type described above, and a cathode situated behind the membrane. A power supply applies a first voltage and a pulse of a second voltage between the cathode and an anode, where the second voltage comprises a voltage which is different from the first voltage. A current detector measures the current between the cathode and the anode in response to the first voltage. As an example, the second voltage may initially be more negative or positive than the first voltage although it may also comprise a voltage which is more positive than the first voltage (or more negative than the first voltage).

Other embodiments include a computer program product carrying a computer program in a non-transitory form. The computer program, when loaded into a processor, may execute a method of the present invention and may be used to control an apparatus of the present invention.

BRIEF DESCRIPTION OF THE DRAWINGS

Embodiments of the invention will now be described with reference to the drawings in which:

FIG. 3 is a graph illustrating performance of an electrode system under different conditions both with and without use of a method of the present invention.

FIGS. 4-6 are similar to FIG. 3 but illustrate performance with and without use of a method of the present invention under various different conditions.

DETAILED DESCRIPTION OF EMBODIMENTS OF THE INVENTION

Figure 1:
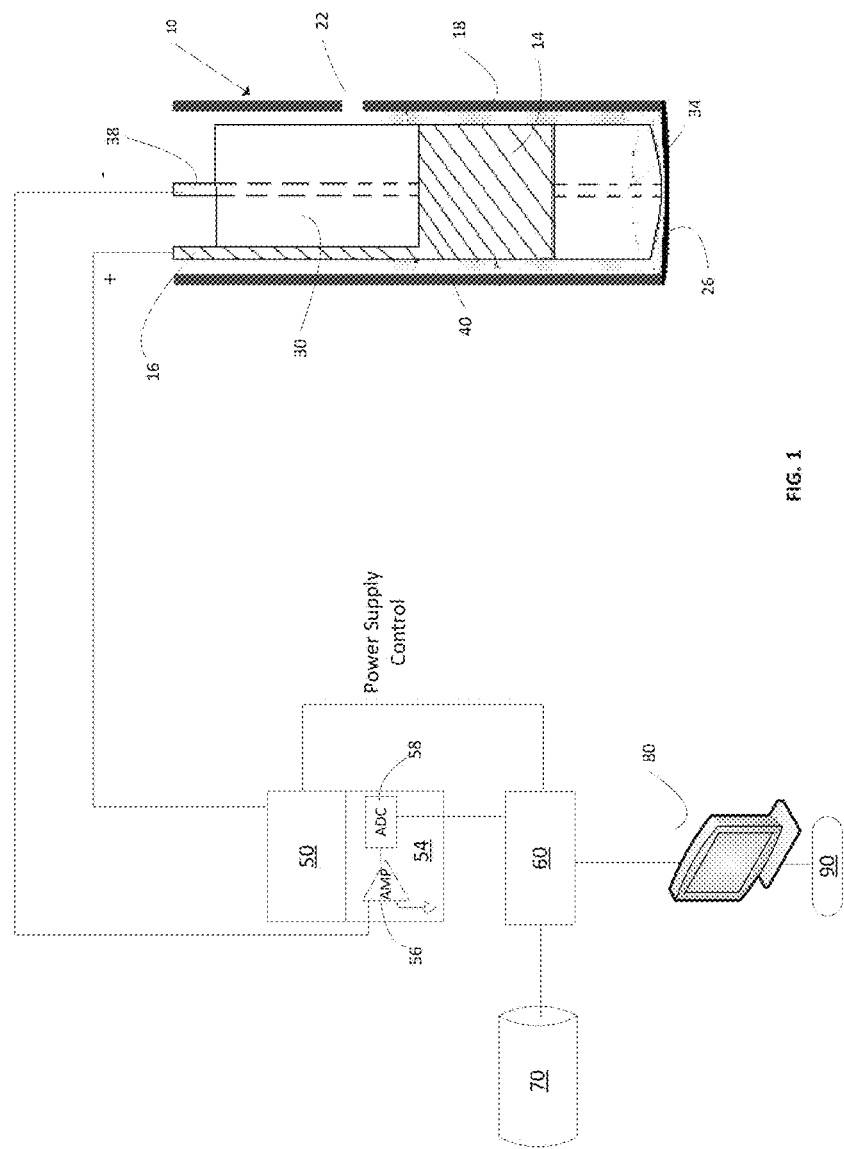
FIG. 1 illustrates an apparatus of an embodiment of the present invention.

In an embodiment of the present invention, the cathode may be gold, platinum, or another noble metal, although other materials, such as carbon and doped diamond, may be used. An anode may be made of any suitable material, such as a material to act as both the reference and counter-electrodes in a two-electrode system, for example silver. However, other materials can be used for the anode or the reference and counter electrodes in a three electrode system or in systems with other numbers of electrodes. The membrane material may be hydrophobic or hydrophilic type. The electrolyte may contain components that facilitate chemical reactions and equilibriums. For example, it can contain be buffered solution containing iodide salts. The electrolyte may also contain polymers to control the viscosity and to control the leaching of active components. The referenced pulse may be applied when the electrode system is in contact with a composition free of detectable species (e.g., a chlorine-free composition) or with a composition containing the detectable species (e.g., a chlorine-containing composition). In some cases, the referenced pulses may be applied repeatedly for a period of time before or between the actual measurements when the electrode system is in contact with a chlorine-free or chlorine-containing composition. For example, the electrode system may be in contact with a chlorine-free or chlorine-containing aqueous composition for a period of at least any one of 10 minutes, 30 minutes, 1 hour, 10 hours or 24 hours, and the pulse of the second voltage may be applied at any time during that period. In another option, the pulse of the second voltage may be combined with the first voltage to form pulse cycle and the cycle may be applied repeatedly and continuously when the electrode system is in contact with the chlorine-free aqueous composition or the chlorine-containing composition. As previously mentioned, the detectable species may be an oxidant such as any halogen, for example, chlorine, iodine or bromine. For example, in seawater, due to the presence of bromide, all chlorine is converted to bromine as a result of chlorine oxidizing bromide. In the detection of bromine the reactions and methods are essentially the same as described herein with hypobromous acid, hypobromite, and bromoamines replacing the corresponding chlorine compounds wherever discussed. This would also be the case for the detection of iodine.

The pulse of the second voltage, or the combined pulse cycle of the first and second voltages may be applied at any time during the period in which the electrode system is in contact with a chlorine-free or chlorine-containing composition. They may also be applied as a single pulse or a series of one or more pulses. In one embodiment the pulses of the second voltages are applied after the electrode system is in contact with the chlorine-free composition for a period of time and prior to collecting measurements for chlorine in the chlorine-containing composition. For example, the pulses of the second voltages may be applied after the electrode system is in contact with the chlorine-free composition for 0.5 to 24 hours but within any of 1 minute, 5 minutes, 30 minutes, 1 hour, or 5 hours before the electrode system is then contacted with a chlorine-containing composition and the first voltage is applied.

It will be understood that when any reference is made in this application to the pulse of the second voltage being applied at certain times, either as a single pulse or a series of pulses, that pulse may be applied only during any of the mentioned times or may also be applied at additional times. Further, the first voltage may also be applied only during the times referenced, or also applied at additional times than when a current is to be measured. For example, the second voltage and the pulse of the second voltage may be applied in an alternating manner as a single waveform, with optionally one or more other voltages applied between them. The single waveform may take on many shapes, and may typically be a rectangular waveform of fixed frequency such as no more than any one of the frequencies between 100 Hz and 3 Hz, for example no more than 5, 10 or 20 Hz.

In some embodiments the membrane of the electrode system is exposed to a chlorine-containing aqueous composition for one period of time and then to a chlorine-free aqueous composition for another period of time, and this sequence repeated. For example, this may occur where the method is used to regularly monitor variations in chlorine at a fixed location in an industrial process. In any such situation where the electrode system is sequentially and repeatedly exposed to chlorine-free and chlorine-containing compositions, multiple pulses of the second voltage may be applied during any one or more or all of the multiple periods during which the membrane is exposed to the chlorine-free aqueous composition. For example, this may be accomplished by either applying one or more pulses of the second voltage during exposure to only the chlorine-free composition, or by applying a waveform of a type already described during at least part or all of each of periods of chlorine-free and chlorine-containing exposure.

Figure 8:
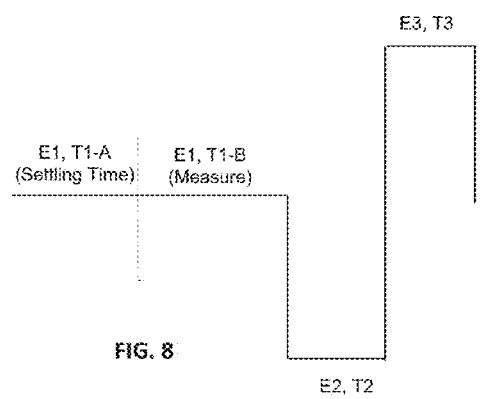
FIGS. 8 and 9 illustrate waveforms that may be used in a method of the present invention.
Figure 9:
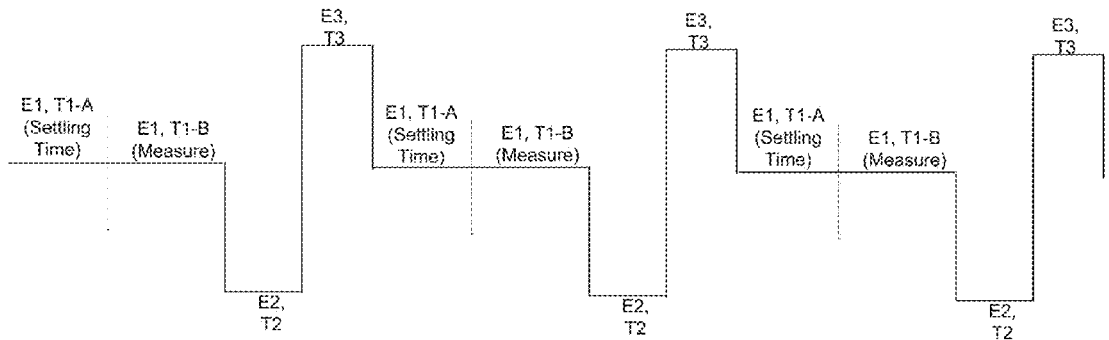

The second voltage is different from the first voltage. It may be composed of a single voltage waveform or of multiple voltage wave forms with multiple steps of voltages and varied duration of each step. For example, in one embodiment of the method, the second voltage is composed of a square voltage step (E2) more negative than the first voltage for duration of T2 followed by another square voltage step (E3) more positive than the first voltage for duration of T3. The second voltage can be combined with the first voltage (E1) of duration T1 to form a full cycle of pulses, as illustrated in FIG. 8. This full cycle of pulses may be applied repeatedly, as illustrated in FIG. 9, at a regular frequency, such as no more than any one of the frequencies between 20 Hz and 0.5 Hz. The second voltage (E2, E3) may deviate significantly from the first voltage. The large excursions are intended to accomplish surface cleaning and reactivation. In embodiments of this invention the idea of PAD is used in a new application where an oxidant is detected at a cathode surface that is indirectly in contact with the sample by a membrane. Embodiments of this invention also propose the use of minor voltage excursions, e.g., ±50-±200 mV away from the first voltage. The minor voltage excursion helps maintain the surface activity especially when analytical measurement signal is near zero while not requiring long recovery time after returning to measurement step at E1. Therefore, measurement may be more continuous.

A wide range of chlorine concentrations may be measured. For example, some embodiments may be used where the chlorine-containing composition is less than any one of 50 ppm, 20 ppm, 10 ppm, 5 ppm, or even less than 1 ppm. Generally, the chlorine-free and chlorine-containing compositions may be aqueous compositions.

Further, in any embodiment parameters may be selected such to shorten the response time T90 which is defined as the time needed to reach 90% of the steady state signal after a change in the concentration from 0 to 1.1 ppm of analyte being measured, such as free chlorine. For example, T90 could be improved from 20 minutes without applying the pulse of the second voltage to less than 5 minutes. In other examples, T90 may be less than 90%, less than 80% or even less than 70% or 60% of the T90 measured under the same conditions but without applying the pulse of the second voltage. For example, the parameters selected to obtain this condition may include the second voltage, the frequency of a waveform which includes a pulse of the second voltage, the total time during which such a waveform is applied, and the elapsed time after application of that waveform and before the electrode is next exposed to a chlorine-containing composition. For example, if T90 was 5 minutes without applying the pulse of the second voltage, then a T90 of less than 70% of that value would be less than 3.5 minutes.

While many embodiments of the invention herein will be described with a cathode and an anode, it will be appreciated that other embodiments may include more than two electrodes. For example, it is well known in that a three electrode system can be configured for amperometric measurements. Such a three electrode system has a working electrode, e.g., cathode, a reference electrode and an auxiliary electrode, e.g., anode, (the latter sometimes is referenced as a counter electrode). Current measured in response to the first voltage is total current through the working electrode, regardless of the number of electrodes.

By a "chlorine-containing" composition is referenced a composition which contains at least 0.5 ppm of chlorine, although they could contain at least 1 ppm, 2 ppm, 3 ppm, 5 ppm or 10 ppm of chlorine. "Free chlorine" references the concentration of hypochlorous acid (HOCl). "Total free chlorine" references the concentration of HOCl and hypochlorite anion (OCl⁻). "Total chlorine" references the sum of the total free chlorine plus the concentration of the chlorine combined with ammonia in the forms of chloramines. With a hydrophobic (gas-permeable) membrane, only the HOCl is detected. To determine total free chlorine based on a measurement of HOCl a pH compensation factor is applied to convert the measured HOCl value to value representing the total of HOCl and OCl⁻. However, with hydrophilic membrane "total chlorine" can be detected. A "chlorine-free" composition is one which is not chlorine-containing (that is zero-chlorine), but may even contain less than 1 ppm or less than 0.5, 0.2 ppm, or 0.1 ppm of free chlorine. In this regard it is well known that molecular chlorine in an aqueous solution will coexist with the other two forms of free chlorine in equilibrium according to the equations:

$$Cl_2 + H_2O = HOCl + H^+ + Cl^- \quad \text{Eq. (1);}$$

pK1=4.6 at 25° C.

$$HOCl = H^+ + OCl^- \quad \text{Eq. (2);}$$

pK2=7.5 at 25° C.

As can be seen from the above, the coexistence of the different forms is pH and temperature dependent. In the situation where the membrane is permeable to only one of the forms, for example HOCl, then the current measured in response to the first voltage represents only the concentration of that form and free chlorine concentration must therefore be calculated back from that measurement in a known manner. pH measurement may be taken such as by a pH sensitive electrode, and a pH compensation can be made in free chlorine calculation in a known manner taking into account Eqs. (1) and (2). Similarly, temperature may be measured and the calculation can be adjusted for the measured temperature.

In any embodiment, an electrode or other item may "comprise" an identified material, such as gold or platinum, or the electrode or other item "is" a particular material such as gold electrode. By "is" in this context allows the material to contain for up to 2%, 5%, 10%, or even 20% or 25% by weight of other materials, such as other metals.

"Measuring", "identifying", "detecting" or similar terms, includes either or both a qualitative evaluation (for example, the substance is or is not present) as well as a quantitative evaluate (that is, how much is present). "May" in this application references something that is optional, for example if an item "may" be present then that means that in one embodiment the item either is present and in another embodiment it is not present. "Or" in this application references any one, or all. For example, if "A or B" is present, then this includes: only A is present; only B is present; both A and B are present. "Contact" or "contacted" or similar terms, are used interchangeably with "expose" or "exposed" or similar terms. All voltages given, unless otherwise indicated, are with reference to the cathode which is held at system ground potential.

A "processor" as used herein may be any hardware or hardware/software combination which is capable of carrying out the steps require of it. For example, a processor may be a suitably programmed microprocessor or application specific integrated circuit. A processor may also include, or be used in conjunction with, a memory of any known type such as a read-only or read-write memory, which holds instructions and data for the operations as described herein. A computer program product referenced herein may include any suitable means for carrying the computer program in a non-transitory form, such as a memory of any configuration, for example a solid state memory or an optical or magnetic memory. The operations or sequences of any method described in the present application can be performed in the order described or in any other order that is logically possible (including, where logically possible, one or more operations being performed simultaneously). All other references cited in this application are incorporated into this application by reference, except to the extent to which they may conflict with the present application in which event the present application prevails. It will be understood throughout this application that some or all of any of the different features described can be combined with each other in different combinations. For example, different ones of the features described under this "Detailed Description" heading, may be used individually or in any combination with the features described under the "Summary" heading.

Figure 2:
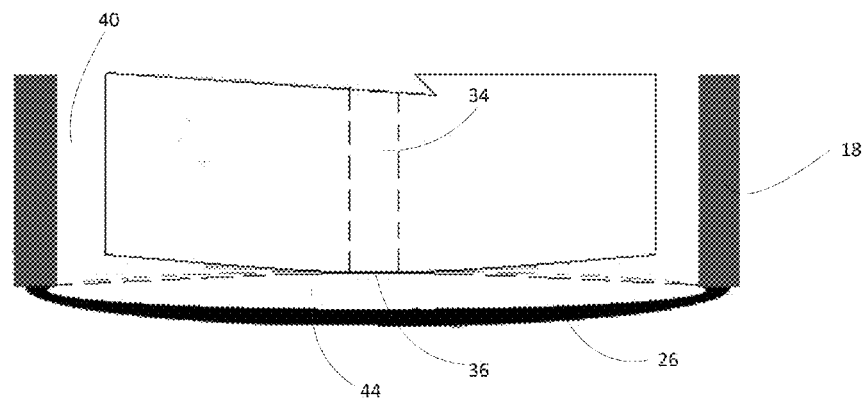
FIG. 2 is an enlarged view of part of FIG. 1 showing in more detail a part of the electrode system.

Referring now to FIGS. 1 and 2, the apparatus shown includes an electrode system 10 with a generally cylindrical outer body 18 having a vent hole 22 on one side. A lower end 6 of outer body 18 is closed by a membrane 26. A solid inner body 30 encloses a gold cathode 34 such that only a lower face 36 of cathode 34 is exposed at a position behind membrane 26 while an upper end 38 is available for an external electrical connection. A cylindrical silver electrode 14 is wrapped around inner body 30, and has an upper end 16 available for an electrical connection. Silver electrode 14 will be the anode and acts as both the reference and counter electrode in the two electrode system shown. As mentioned before though, separate reference and counter electrodes can be used in a three electrode system. Note that there is a gap 40 between inner body 30 and outer body 18, as well as an almost invisible gap 44 between face 36 and membrane 26. Gap 40 is filled with a reference electrolyte to cover the whole electrode 14. Suitable reference electrolytes include halide salt (e.g., KCl) solution at a 0.1 M concentration. Gap 44 may or may not be visible but exists to allow electric continuity between working electrode and the reference and counter electrode, especially when reference electrode and counter electrode are behind the membrane. Outer and inner bodies 18, 30 will be made of an inert material, such as a plastic or glass. Membrane 26 may be a semi-permeable membrane with high permeability to one or more of molecular chlorine ($Cl_2$), hypochlorous acid (HOCl), or hypochlorite anion ($OCl^-$), and may have low permeability to other species. It can also functions as a filter to discriminate certain particles. Examples of suitable materials for membrane 26 include hydrophobic type, such as polytetrafluoroethylene ("PTFE"), polyvinylidene fluoride ("PVDF"), and hydrophilic type, such as polyethersulfone (PES), polycarbonate (PCTE), Polyvinylidene fluoride (PVDF). Since membrane 26 is delicate, a mesh (not shown) of suitable material may be provided for support.

Electrode system 10 is connected to a power supply 50 and current detector 54, which includes analog-to-digital converter 58, and op amplifier 56 connected between cathode 38 and ground. Power supply 50 applies the first voltage and the pulse of the second voltage across cathode 34 and anode 14, while current detector 54 measures the cathode current. A processor 60 controls power supply 50 and converts current readings from current detector 54 into total free chlorine readings for presentation on display 80 and/or storage in memory 70. This operation may be in accordance with computer program code stored in memory 70 and in response to operator input received at input device 90. Power supply 50 may provide the first voltage and a pulse of the second voltage in accordance with any of the various programs described below, or any other suitable program.

Figure 7:
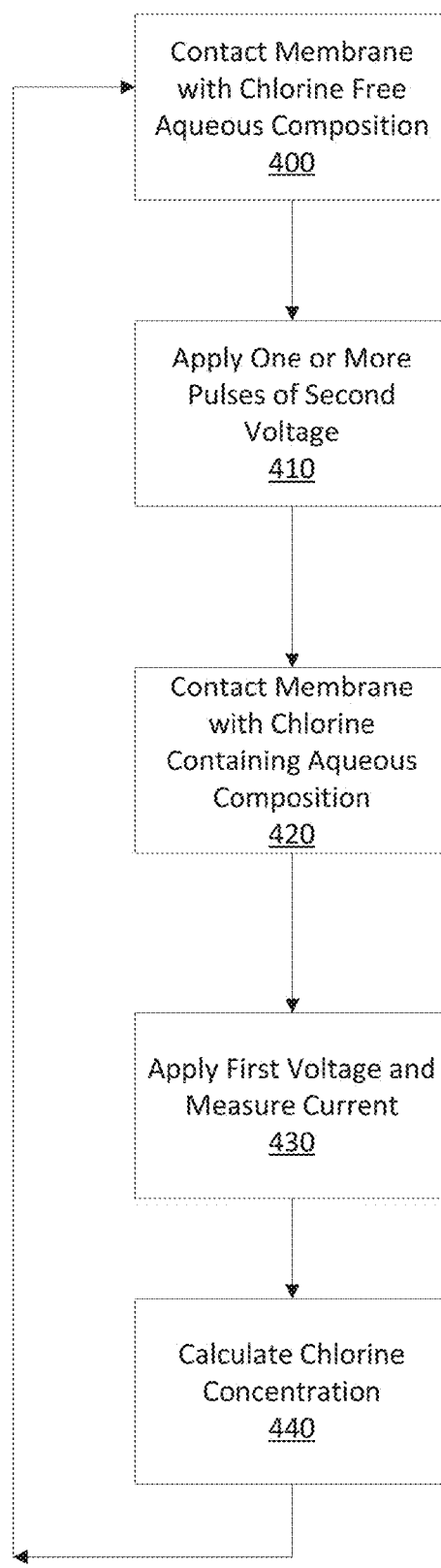
FIG. 7 is a flowchart illustrating a method of the present invention.

The apparatus of FIGS. 1 and 2 may be used in an embodiment of a method of the present invention. One method may be applied according to FIG. 7 in which the membrane 36 of the electrode system is contacted (400) with a chlorine-free aqueous solution. One or more pulses of a second voltage may be applied (410) during this period of contact. Membrane 36 is then contacted (420) with a chlorine-containing aqueous solution during which period a first voltage may be applied (430) and the resulting current measured (430). Processor 60 may calculate total free chlorine using the measured current and any pH and temperature readings from sensors (not shown). The membrane of the electrode system may again be contacted (400) with a zero-chlorine aqueous composition and the cycle (400-440) then repeated one or more times with a same or different chlorine-containing solution and same or different first and second voltages and their application parameters.

While not being intended to limit the present invention to any specific electrochemical mechanism, it is believed that in a 2-electrode system the processes occurring during step 430 may be as follows. Namely, while the first voltage is applied and the current is being measured (430), chlorine species (e.g., hypochlorous acid HOCl) diffuses through membrane 26 and is reduced at the cathode according to Eq. (3) below. A diffusion limited equilibrium concentration between face 36 of gold cathode 34 and membrane 26 is reached.

$$HOCl + H^+ + 2e^- = Cl^- + H_2O \quad\quad \text{Eq. (3)}$$

At the silver electrode (anode), silver is oxidized into $Ag^+$ ions which may then precipitate with the halide ions (e.g., $Cl^-$) present in the electrolyte according to Eq. (4) below:

$$2Cl^- + 2Ag = 2AgCl + 2e^- \quad\quad \text{Eq. (4)}$$

The HOCl reduction at the cathode generates a current which is directly proportional to its concentration when diffusion is under control.

In a case that the membrane is hydrophilic, more than one form of chorine species may diffuse through the membrane. In some applications, the electrolyte behind the membrane may contain chemicals to convert all the forms of chlorine to become one type of oxide to be detected at the cathode. For example, if the electrolyte contains iodide (I$^-$), chlorine may convert iodide to iodine ($I_2$) and the latter then is reduced at the cathode quantitatively.

Examples 1-3

In Example 1 the electrode system of FIGS. 1-2 was left in continuous contact with a zero-chlorine aqueous buffer solution of pH 6.1 for 1 day, during which time a first voltage of –100 mV was applied across the electrodes and the current was near zero. The electrode system was then placed in contact with a chlorine-containing aqueous buffered to a pH 6.1 and containing approximately 1.64 ppm of free chlorine. The current in response to the first voltage (sometimes referenced as a "data read voltage") was measured and is shown as plot 100 in FIG. 3. Time=0 represents the time of first exposure to chlorine-containing solution. The plateau representing a current reading which is sufficiently stable to provide an accurate calculation of free chlorine in a calibrated system, was reached at a current reading of about 570 nA and was achieved only after about 40 mins. The T90, represented by position 104, was not reached until about 20 minutes. This means that anywhere from Time=0 to Time of about 20-40 minutes any current reading taken on a calibrated system could not be reliably used to calculate free chlorine. Note that in Example 1 the electrode was then in contact with zero-chlorine solution for about 10 minutes at position 108 (Time equals about 40 minutes) resulting in the zero current reading of plot 100 beginning at about 40 minutes. However this short period exposure to zero-chlorine solution did not have profound effect on the electrode. The electrode responded to chlorine relatively quickly with T90 being less than 4 mins. with the testing setup.

In Example 2, the protocol of Example 1 was repeated except: the electrode system was in continuous contact with the zero-chlorine buffer solution for 2 days and then contacted with the chlorine-containing solution containing 1.54 ppm of free chlorine; and the electrode was in contact with zero-chlorine buffer solution at Time equals about 30 minutes for a period of about 10 minutes. The current measured in response to the read voltage is shown as plot 120 in FIG. 3. It can be seen from plot 120 that the T90 was about 20 minutes while the plateau was not reached until about 70 minutes after contact with the chlorine-containing solution.

In Example 3 the protocol of Example 1 was repeated except the electrode system was in contact with the chlorine-free buffer solution overnight during which time a program of pulses of the second voltage were applied.

TABLE 1

| | |
|---|---:|
| Pulse voltage E2 (mV) (anode vs cathode) | –250 |
| Pulse duration T2 (sec) | 1 |
| Pulse voltage E3 (mV) (anode vs cathode) | 760 |
| Pulse duration T3 (sec) | 1 |
| Frequency (Hz) | 0.5 |

After applying the pulse program as set out in Table 1, the electrode system was then placed in contact with the chlorine-containing solution and the first voltage (the data read voltage) was again applied and the resulting current read. The current measured in response is shown as plot 140 of FIG. 3. Note that the electrode was dipped in zero-chlorine buffer solution in this Example 3 twice (at Time equals about 30 mins and 60 mins). It will be seen from plot 140 that after using pulse program of Table 1, the T90 was only about 5 minutes while the plateau was reached in less than 10 minutes, much faster than in the case of Examples 1 or 2. Similarly, after exposing to zero-chlorine buffer solution for short time period then returning to the chlorine solution at about Time of 45 and 67 mins, the measured current rapidly reached its maximum value, indicating that short term exposure to zero-chlorine did not have any significant impact.

Examples 4, 5

Example 4 followed the same protocol as Example 1, except the electrode system was exposed to the zero-chlorine buffer solution for only 4 hours. At Time 0, the electrode system was back in contact with a 1.15 ppm free chlorine solution at pH 6.1. The resulting current is shown as plot 160 in FIG. 4. Note that the T90 was 8 minutes followed by a relatively long rise to an eventual plateau value at about 20 minutes.

Example 5 followed the same protocol as Example 1 except that after the electrode being running in zero-chlorine buffer under the first voltage for 20 hours, a pulse of a second voltage of the same program of Table 1 was applied for 5 minutes while the electrode system was in contact with the chlorine-free buffer solution before Time 0. At Time 0 the read voltage was applied while the electrode system was in contact with a 1.15 ppm free chlorine solution at pH 6.1. The resulting current is shown as plot 180. Note that T90 of plot 180 was only about 3.3 minutes.

Example 6

Example 6 followed the same protocol as Example 5 except the electrode system was maintained in contact with the zero-chlorine buffer solution over a weekend, and the pulses of the second voltage were applied according to the protocol of Table 2 for 5 minutes before the electrode system was contacted with a chlorine containing solution (0.89 ppm free chlorine) and the first voltage was applied. Additionally, the electrode system was in contact with zero-chlorine solution (at Times of about 14 and 29 minutes).

TABLE 2

| | |
|---|---|
| Pulse voltage E2 (mV) (anode vs cathode) | −200 |
| Pulse duration T2 (sec) | 5 |
| Pulse voltage E3 (mV) (anode vs cathode) | 780 |
| Pulse duration T3 (sec) | 5 |
| Frequency (Hz) | 0.1 |

The resulting current is shown as plot 200 of FIG. 5. Note again the short T90 of about 4 minutes after the read voltage was initially applied, and less than 2 minutes and about 3 minutes after a short term contact with zero-chlorine buffer solution and back to the chlorine solution at about Times of 18 minutes and 41 minutes.

Examples 7-8

Examples 7-8 followed the same protocol as Example 1 except as noted in the following. The resulting current measurements are shown as plots 220 and 240 in FIG. 6. In the case of plot 220, the electrode system was left for 2 days in continuous contact with the zero-chlorine buffer solution under the first voltage, the measured current being zero. Second voltage pulses according to Table 3 were then applied for 5 minutes prior to Time 0. At Time 0 the electrode system was placed in contact with 1.31 ppm free chlorine in buffer at pH 6.1. In the case of plot 240, the electrode system was left for overnight in continuous contact with the zero-chlorine buffer solution under the first voltage and then at Time 0 was in contact with ~1.1 ppm chlorine buffer without change in voltage. That is, in plot 240 no pulses of the second voltage were applied. It will be seen from a comparison of plots 220 and 240, that again the use of the pulses of the second voltage resulted in a considerably lower T90 than when no pulses were used, and plateau current levels were achieved in a shorter Time.

TABLE 3

| | |
|---|---|
| Pulse voltage E2 (mV) (anode vs cathode) | −200 |
| Pulse duration T2 (sec) | 1 |
| Pulse voltage E3 (mV) (anode vs cathode) | 1100 |
| Pulse duration T3 (sec) | 1 |
| Frequency (Hz) | 0.5 |

Other pulse programs may be used than those described above. For example, a single waveform as shown in FIG. 8 might be applied, or the waveform of FIG. 8 could be repeated at a frequency of 0.5-20 Hz as shown in FIG. 9. Such a waveform of FIG. 9 may have the parameters listed in Table 4 or Table 5 below and may be applied during part or all of the time the electrode system is exposed to the zero-chlorine or chlorine-containing aqueous solution. For example, such a waveform may be continuously applied while the electrode system is cycled through repeated periods of contact with zero-chlorine and chlorine containing solutions. In FIGS. 8 and 9 current data may be taken at E1 (the "data read" or "first voltage") during time T1-B after a delay of T1-A, e.g., 1000 ms, to allow the system to stabilize. E2 and E3 represent the pulse voltage ("second voltage").

TABLE 4

| | |
|---|---|
| E1 (mV) (anode vs cathode) | −100 |
| T1 (ms) | 1300 |
| E2 (mV) (anode vs cathode) | −200 |
| T2 (ms) | 100 |
| E3 (mV) (anode vs cathode) | 0 |
| T3 (ms) | 100 |

TABLE 5

| | |
|---|---|
| E1 (mV) (anode vs cathode) | −100 |
| T1 (ms) | 1300 |
| E2 (mV) (anode vs cathode) | −600 |
| T2 (ms) | 80 |
| E3 (mV) (anode vs cathode) | 1100 |
| T3 (ms) | 80 |

Other examples in which an apparatus and methods of any of the above type can be used include those of below:
  a. Electrode system is in continuous contact of chlorine solution.
  b. Electrode system is in contact with low chlorine (e.g., <0.1 ppm) or zero-chlorine solution for more than 4 hours.

c. Electrode system is in contact with contaminants that may deteriorate the activity of the cathode.

Pulse programs may be flexible to include multiple voltages of multiple time periods, as shown in FIGS. 8 and 9. For example, E2 and E3 may be in the range of −1200 mV to +1200 mV, pulse frequency may be 0.1 to 1 Hz. Pulse programs may be applied for a fixed time periodically, e.g., 5 minutes every 12 hours; or right before measurement is started, e.g., 5 minutes before measurement is started. Pulse programs may also be applied constantly when the system is measuring chlorine, whether or not in chlorine containing solution or in zero chlorine solution.

Particular embodiments of the present invention have been described in detail above. For example, any of the embodiments might be used for chlorine dioxide, bromine, and total oxidant detection. However, it will be apparent that variations and modifications of the described embodiments are possible. Accordingly, the present invention is not limited by the embodiments described.

The invention claimed is:

1. A method of measuring oxidant in an aqueous composition using an electrode system comprising a membrane permeable to a species to be measured, a cathode situated behind the membrane, and an electrolyte between the membrane and cathode, the method comprising:
    contacting the membrane and an anode with the aqueous composition and measuring the current between the cathode and anode in response to a first voltage applied between them;
    applying a pulse of a second voltage between the cathode and the anode, where the second voltage is different from the first voltage.

2. A method according to claim 1 wherein the cathode is comprised of gold or platinum.

3. A method according to claim 1 wherein the pulse is applied when the electrode system is in contact with a chlorine free aqueous composition.

4. A method according to claim 3 wherein the electrode system is in contact with the chlorine free aqueous composition for at least 1 hour and the pulse of the second voltage is applied during that time.

5. A method according to claim 3 wherein the pulse of the second voltage is applied repeatedly during a time in which the electrode system is in contact with the chlorine free aqueous composition.

6. A method according to claim 3 wherein the electrode system is in contact with the chlorine free aqueous composition for at least 5 hours and the pulse of the second voltage is applied during that time.

7. A method according to claim 1 additionally comprising sequentially and repeatedly exposing the membrane to a chlorine containing aqueous composition and a chlorine free aqueous composition, and wherein multiple pulses of the second voltage are applied during each of multiple periods during which the membrane is exposed to the chlorine free aqueous composition.

8. A method according to claim 4 additionally comprising applying multiple pulses of the second voltage during each of multiple periods of exposure to the chlorine containing composition.

9. A method according to claim 4 wherein the second voltage comprises a voltage which is initially more negative than the first voltage.

10. A method according to claim 4 wherein the total chlorine concentration of the chlorine containing composition is less than 20 ppm.

11. A method according to claim 4 wherein the pulses of the second voltage comprises a voltage which differs from the first voltage by less than 200 mV.

12. A method according to claim 4 wherein the voltage pulses are applied at a frequency of no more than 10 Hz.

13. A method according to claim 1 wherein a T90 in response to the first voltage is less than 70% of the T90 measured under the same conditions but without applying the pulse of the second voltage, the T90 being defined as the time needed to reach 90% of a steady state signal after a change in a concentration from 0 ppm to 1.1 ppm of the oxidant.

14. A computer program product carrying a computer program in a non-transitory form which program, when loaded into a processor, executes a method of measuring free chlorine in an aqueous composition comprising:
    applying a first voltage between an anode and a cathode having an aqueous composition therebetween;
    measuring the current between the anode and cathode in response to the first voltage applied between them;
    calculating free chlorine concentration of the aqueous composition based on the measured current;
    applying a pulse of a second voltage between the anode and cathode, wherein the second voltage comprises a voltage which is initially more negative than the first voltage.

15. A computer program product according to claim 14 wherein a sequence of alternating first and second voltages are applied at a frequency of no more than 10 Hz.

16. A computer program product according to claim 14 wherein the calculating free chlorine comprises calculating total free chlorine.

* * * * *

UNITED STATES PATENT AND TRADEMARK OFFICE
CERTIFICATE OF CORRECTION

PATENT NO. : 9,664,636 B2
APPLICATION NO. : 14/138933
DATED : May 30, 2017
INVENTOR(S) : Xiaowen Wen et al.

It is certified that error appears in the above-identified patent and that said Letters Patent is hereby corrected as shown below:

On the Title Page

Page 2, (56) References Cited, Other Publications, Line 25, change "Coloimetric" to --Coulometric--.

In the Drawings

On Sheet 3 of 7, FIG. 3, Line 3, change "buffer for 2 day" to --buffer for 2 days--.

On Sheet 3 of 7, FIG. 3, Line 4, change "ppmchlorine" to --ppm chlorine--.

In the Specification

In Column 3, Line 18, change "For example, it can contain be buffered solution containing iodide salts." to --For example, it can be buffered solution containing iodide salts.--.

In Column 5, Line 19, change "For example, it is well known in that a three electrode system" to --For Example, it is well known that a three electrode system--.

In Column 6, Line 5, change "to contain for up to 2%, 5%," to --to contain up to 2%, 5%,--.

In Column 7, Line 10, change "It can also functions as a filter" to --It can also function as a filter--.

In Column 7, Line 62, change "HOCl + H$^+$ + 2e$^-$ = Cl$^-$ + H2O Eq. (3)" to --HOCl + H$^+$ + 2e$^-$ = Cl$^-$ + H$_2$O Eq. (3)--.

In Column 8, Line 57, change "the second voltage were applied" to --the second voltage was applied.--.

Signed and Sealed this
Fifteenth Day of August, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,664,636 B2

In the Claims

In Column 12, Claim 11, Line 18, change "wherein the pulses of the second voltage comprises a voltage" to --wherein the pulses of the second voltage comprise a voltage--.

In Column 12, Claim 15, Line 45, change "wherein a sequence of alternating first and second voltages are applied" to --wherein a sequence of alternating first and second voltages is applied--.